United States Patent [19]
Lieber et al.

[11] Patent Number: 5,437,637
[45] Date of Patent: Aug. 1, 1995

[54] TRANSPORT CATHETER

[75] Inventors: Clement E. Lieber, Yorba Linda; Miriam H. Taimisto, Sierra Madre; Mark A. Konno, Costa Mesa, all of Calif.

[73] Assignee: Baxter International Inc., Deerfield, Ill.

[21] Appl. No.: 83,105

[22] Filed: Jun. 24, 1993

Related U.S. Application Data

[62] Division of Ser. No. 790,724, Nov. 8, 1991, Pat. No. 5,246,016.

[51] Int. Cl.$^6$ .............................................. A61M 29/00
[52] U.S. Cl. ..................... 604/96; 604/264; 604/280; 606/192; 606/194; 128/673; 128/692; 128/736
[58] Field of Search ............... 604/43, 45, 96, 264, 604/280; 606/192, 194; 128/656, 658, 673, 692, 736

[56] References Cited

U.S. PATENT DOCUMENTS

| | | | |
|---|---|---|---|
| 3,499,435 | 3/1970 | Rockwell et al. | 128/2.05 |
| 3,981,299 | 9/1976 | Murray | 604/43 |
| 4,406,656 | 9/1983 | Hattler et al. | 604/280 |
| 4,582,067 | 4/1986 | Silverstein et al. | 128/663 |
| 4,613,323 | 9/1986 | Norton et al. | 604/43 |
| 4,733,669 | 3/1988 | Segal | 128/663 |
| 4,755,176 | 7/1988 | Patel | 604/280 |
| 4,757,821 | 7/1988 | Snyder | 128/660 |
| 4,796,640 | 1/1989 | Webler | 128/736 |
| 4,813,429 | 3/1989 | Eshel et al. | 604/43 |
| 4,841,981 | 6/1989 | Tanabe et al. | 128/692 |
| 4,892,519 | 1/1990 | Songer et al. | 606/194 |
| 4,901,734 | 2/1990 | Griffin et al. | 128/692 |
| 5,025,778 | 6/1991 | Silverstein et al. | 128/4 |
| 5,176,144 | 1/1993 | Yoshikoshi et al. | 128/736 |
| 5,308,319 | 5/1994 | Ide et al. | 604/280 |

FOREIGN PATENT DOCUMENTS 0303756  2/1989  European Pat. Off. .
WO89/00023  1/1989  WIPO .

Primary Examiner—C. Fred Rosenbaum
Assistant Examiner—N. Kent Gring
Attorney, Agent, or Firm—Bruce M. Canter

[57] ABSTRACT

A catheter with several independent lumens extending longitudinally through the catheter for accepting probes and for introducing fluid through the catheter and into a body cavity is disclosed. The catheter outer body has a cross-sectional maximum outer dimension. The first lumen is circular in cross-section, and has a cross-sectional dimension of approximately half the maximum outer dimension of the catheter body. The first lumen is capable of accepting various probes, as well as allowing simultaneous fluid flow through the lumen. The second lumen is crescent-shaped in cross-section and occupies at least a quarter of an arc around the cross-section of the catheter body. The large cross-section of the second lumen allows for a high fluid flow rate through the lumen. The third lumen allows for inflation of an inflation balloon (when present), and the fourth lumen allows for the passing of a portion of an instrument along the length of the lumen.

23 Claims, 2 Drawing Sheets

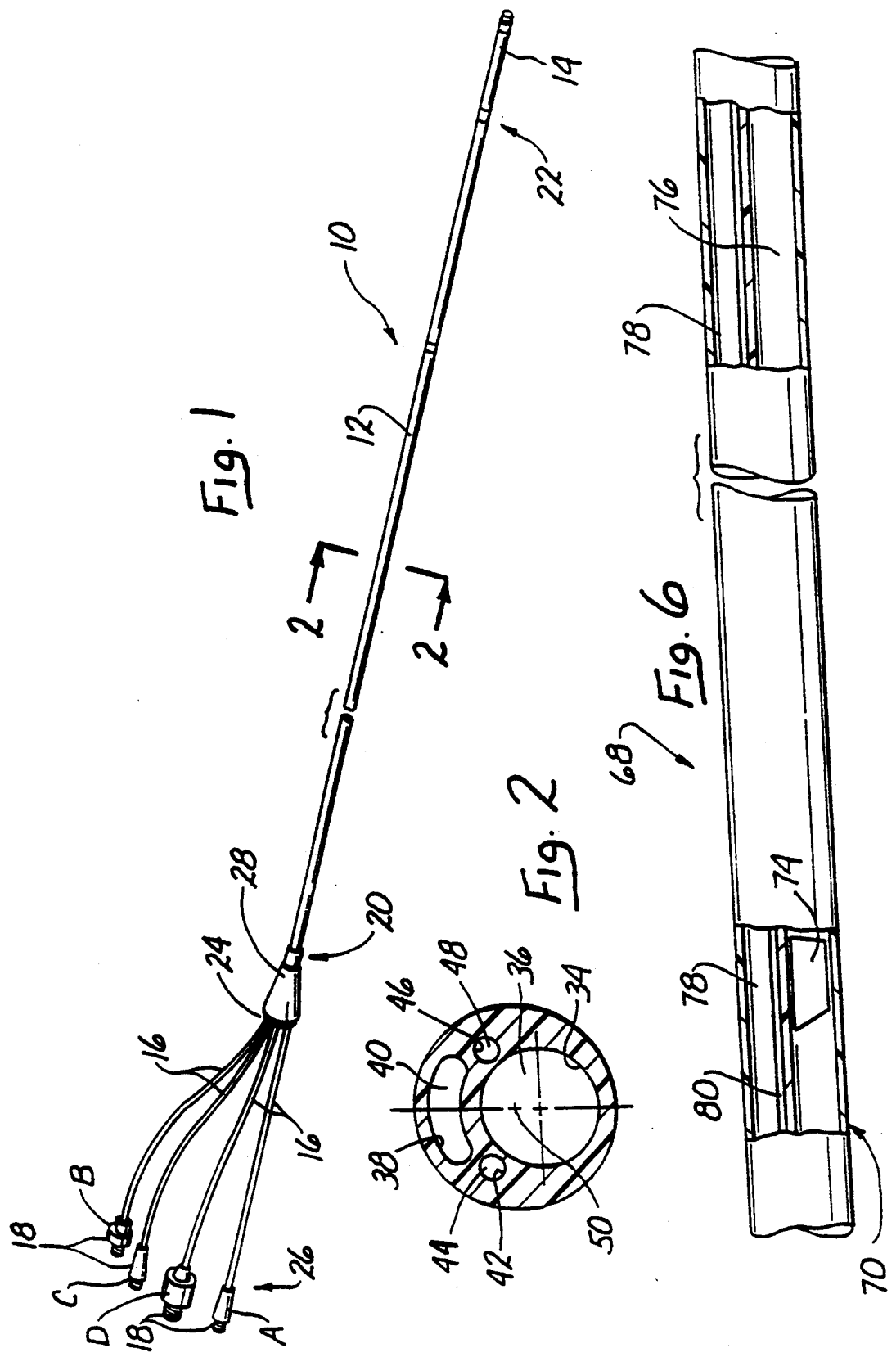

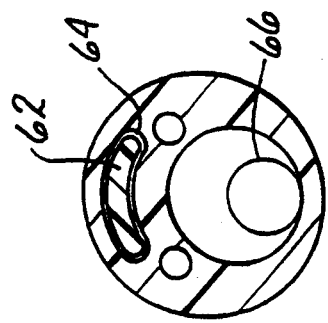
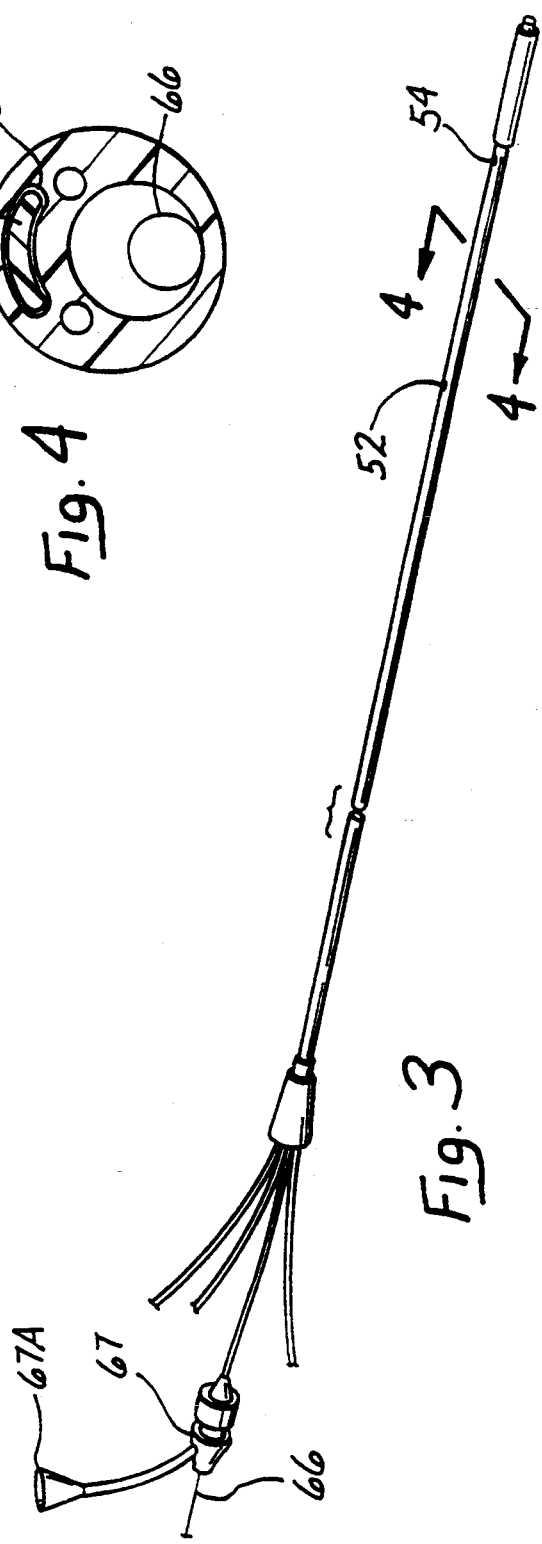
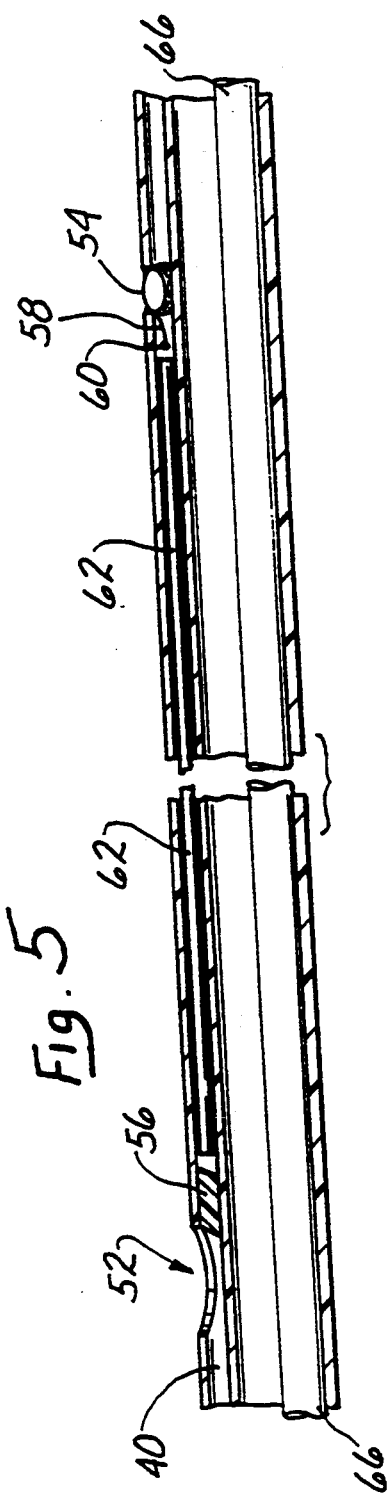

TRANSPORT CATHETER

This application is a divisional of U.S. application Ser. No. 07/790,724, filed on Nov. 8, 1991 (now U.S. Pat. No. 5,246,016).

BACKGROUND OF THE INVENTION

1. Field of the Invention

The present invention relates to an improved transport catheter, and more particularly to an improved catheter which can accept various probes for sensing biological conditions and parameters and which allows high fluid flow rate for introducing fluids irrespective of the presence of sensing instruments in the catheter, thereby reducing the risk of patient complications.

2. Description of the Prior Art

Numerous catheters exist for sensing, diagnosing and treating various biologic conditions. For example, there are cardiac catheters used for angioplasty, for measuring cardiac output, such as thermodilution catheters, pulmonary artery wedge pressure monitors, blood flow monitors and temperature monitors. In use, a transport catheter is initially introduced into an appropriate vessel or body cavity. In the case of a thermodilution catheter, for example, the transport catheter may be introduced into an appropriate vein. Thereafter, the thermodilution catheter is inserted and passed through the right atrium and ventricle and out to the pulmonary artery. After the catheter is properly positioned and the balloon inflated, various readings can be taken of left heart pressure, for example, and pulmonary artery temperature. The same measurements may be taken a number of times while the catheter is in place. However, if the patient's condition changes and requires other measurements or diagnosis, or additional information is desired, such as may be required in view of the results obtained by the thermodilution measurements, the thermodilution catheter must be removed and substituted with a different catheter for such measurements. The subsequent catheter exchange increases the possibility of infection through the introduction of a second catheter and increases the probability of other problems such as venous puncture.

Thermodilution catheters, such as the well known Swan-Ganz catheters, generally provide for introducing fluids into the patient through the catheter. However, some procedures require higher fluid flow rates or introduction of more viscous fluids than are presently contemplated with such catheters. Such catheters are generally not designed for maximum fluid flow or for efficient flow of relatively viscous fluids.

In the past, multi-lumen catheters were designed wherein the catheter body was divided into circular sections of similar size or substantially triangular sections to form the separate lumens. These catheters were generally too small to accept sensing probes and one or more of the lumens of such catheters occasionally become constricted at the seal of the transport catheter. A further disadvantage of these multi-lumen catheters becomes apparent if an ultrasound probe was to be used within one of the lumens of the catheter in order to obtain diagnostic readings. In this case, the similar sized lumens surrounding the probe-carrying lumen contain relatively large amounts of air space that cause undesirable attenuation of the ultrasonic signal.

There is therefore a need for an improved catheter which can accept a variety of successive probes or sensors or other instruments and which also, simultaneously, allows for high fluid flow for fluids to be introduced into the body, as well as the introduction of relatively viscous fluids. Additionally, a need also exists for a multi-lumen catheter that minimizes the sizes of the lumens which might contain ultrasonic wave attenuating air in lumens adjacent an instrument containing lumen.

SUMMARY OF THE INVENTION

One object of the present invention is to provide a transport catheter that provides a plurality of lumens for accepting various sequential probes through at least one of the lumens without requiring the insertion and removal of a different catheter with each probe.

Another object of the present invention is to provide a transport catheter with a plurality of lumens that allows for increased fluid flow rate through at least one of the lumens.

A still further object of the invention is to provide a transport catheter with a plurality of lumens that allows fluid flow through at least one of the lumens with a probe inserted in the lumen.

Yet another object of this invention is to provide a transport catheter with a plurality of lumens that allows for an increased accuracy in ultrasound readings by minimizing the attenuation of the signal caused by the quantity of air space in the surrounding lumens.

Still another object of the present invention is to provide an improved pulmonary artery or central venous transport catheter with a plurality of lumens wherein one lumen is an inflation lumen used to inflate an inflation balloon.

Yet another object of the present invention is to provide a transport catheter with a plurality of lumens wherein one lumen allows for the passing of a portion of an instrument along the length of the lumen, such as thermocouple wires, for example.

These and other objects of the present invention are achieved through a catheter comprising a catheter body having an outer edge with an outer dimension and having a proximal end and a distal end. The body also includes walls defining, in transverse cross-section, a plurality of lumens extending longitudinally substantially through the catheter body including a first wall defining a first lumen having a first transverse dimension approximating about half of the dimension of the catheter body. A second wall defines a curved lumen wherein the lumen occupies at least a quarter of an arc around the catheter body. With this configuration, the catheter can serve multiple functions. The first lumen can serve not only as a probe lumen for transporting a suitable probe or sensor, but also as a lumen for introducing fluids, sensing fluid pressure and taking fluid samples. The second lumen is preferably formed so as to maximize the cross-sectional area for fluid flow while still maintaining sufficient catheter structural integrity to be reliable under a wide variety of conditions. The second lumen allows introduction of fluids at relatively high flow rates, or fluids with viscosities higher than normal, such as those which may be more viscous than saline. The first lumen is preferably circular to accept a wide range of probes.

In a further form of the invention, a third wall is included defining an inflation lumen for inflating and deflating an inflation balloon mounted at the distal end of the catheter body, and a fourth wall is included defining an instrument lumen for passing a portion of an instrument along the lumen.

A catheter according to this embodiment of the invention having an inflation balloon, an inflation lumen and a fourth lumen can be used as a typical Swan-Ganz type of catheter for thermodilution measurements. The first lumen is used for sensing pressure and the like while the curved lumen serves as an injection lumen. The inflation lumen is relatively small and serves the standard function, while the fourth lumen can carry the thermocouple wires. If a further test or procedure is then necessary, for example as a result of the outcome of the thermodilution measurements, a probe can be inserted into the first, probe lumen as necessary. Additional tests may require other probes, all of which can in turn be introduced without removing the catheter, and without significant additional risk to the patient.

The above described objects and other objects of the present invention will now become apparent from a review of the drawings and the following description of the preferred embodiments.

BRIEF DESCRIPTION OF THE DRAWINGS

FIG. 1 is a perspective view of the transport catheter of the present invention.

FIG. 2 is a cross-sectional view of the transport catheter of the present invention taken along line 2—2 of FIG. 1.

FIG. 3 is a perspective view of a catheter according a further embodiment of the present invention showing a probe and an injectate port.

FIG. 4 is a transverse cross-sectional view of the catheter of FIG. 3 taken along line 4—4.

FIG. 5 is a longitudinal cross-sectional view of a portion of the catheter of FIG. 3.

FIG. 6 is a partial segmented side-sectional view of a catheter according to a further embodiment of the present invention.

DETAILED DESCRIPTION OF THE PREFERRED EMBODIMENTS

Referring now to FIG. 1, a catheter 10 for accepting probes and for introducing fluid through the catheter and into a body cavity is shown which allows numerous procedures to be done using a single catheter and which reduces the likelihood of injury to the patient. In one preferred embodiment, the catheter 10 is primarily comprised of a catheter body 12, an inflation balloon 14, a plurality of extension tubes 16, and a plurality of threaded hubs 18. The catheter body 12 has a proximal end 20 and a distal end 22. The inflation balloon 14 is mounted to the catheter body 12 at the distal end 22 of the catheter body 12 as would be known to one skilled in the art. Each of the extension tubes 16 has a respective first end 24, which is coupled to a corresponding one of a plurality of lumens (shown in FIG. 2) in the catheter body 12 at the catheter body proximal end 20 at a backform 28. The extension tubes 16 provide access to each of the respective lumens. The extension tube corresponding to the first lumen, described more fully below, also includes graduations on the outside of the tube to indicate the depth of insertion of any probe or instrument passed along the first lumen. The second end 26 of each of the extension tubes 16 is coupled to a respective one of the plurality of threaded hubs 18. The threaded hubs 18 each have a luer taper common in the art for connecting suitable instruments, such as probe connectors, an inflation device for the inflation balloon and an injection device for the injectate lumen described more fully below.

Referring now to FIG. 2, a cross-sectional view of the catheter body 12 is shown taken at an approximate mid-point of the catheter body. A plurality of walls within the catheter body 12 define the respective plurality of lumens. A first wall 34 defines a first lumen or probe lumen 36. The cross-sectional configuration of the probe lumen 36 is preferably circular, and has a diameter in the preferred embodiment of approximately half the diameter of the cross-section of the catheter body 12. A second wall 38 defines a second lumen or an injectate lumen 40. In the preferred embodiment shown in FIG. 2, the cross-section of the injectate lumen 40 is crescent-shaped. A suitable size for the second lumen is one where it occupies at least a quarter of an arc around the cross-section of the catheter body 12. A third wall 42 defines a third, inflation lumen 44, in cross-section preferably circular, and a fourth wall 46 defines a fourth lumen 48, also preferably circular.

The probe lumen has a large cross-sectional area and preferably occupies a significant portion of the cross-sectional area of the catheter so that the catheter can accept as many different types and configurations of probe as possible and to permit a wide variety of tasks or procedures without having to remove the catheter. The probe lumen is also preferably large enough to permit fluid flow within the lumen even while a probe or other element is in the probe lumen. This allows simultaneous instrument sensing and pressure monitoring or introduction of fluid such as pharmaceuticals through the probe lumen, even with concurrent introduction or withdrawal of fluid through the injectate lumen 40. In this manner, removal of the probe is not required before injectate can be introduced or blood withdrawn through the probe lumen. Fluid pressure can also be monitored even while a probe is in place in the lumen 36. For example, the lumen 36 is capable of accepting hemoglobin oxygen saturation probes, pacing probes, cardiac output probes, right heart ejection fraction probes, right heart ejection fraction with hemoglobin oxygen saturation probes, hemoglobin pH probes, and high fidelity pressure monitoring probes. A preferred probe configuration is circular in external dimension. In one preferred form of the invention having the four lumens as described, a 7½ French catheter has a 0.056 inch diameter probe lumen and the probes are preferably around 0.042 inches in diameter.

The advantage of the probe substitution feature of the probe lumen 36 is apparent from a description of the use of the catheter 10. In use, the catheter body 12 is first inserted and properly positioned in the body. A selected probe is then inserted through the probe lumen 36 of the catheter body 12 and the desired procedure is carried out. Thereafter, another type of probe measurement may be required such as where the patient's condition changes. The first probe is then removed from the catheter body 12, leaving the catheter body 12 in place, and a second probe is inserted through the probe lumen 36 of the catheter body 12 in order to accomplish a different probe function. The insertion and removal of the catheter body with each type of probe is avoided. As a result, there is significantly less risk to the patient of infection from the repeated insertion and removal of catheters, as well as less risk of venous puncture or other problems.

The large cross-sectional area of the injectate lumen 40 allows for a high fluid flow rate through the lumen, and also accommodates the flow of relatively viscous fluids. Therefore, the second lumen 40 is well-suited for procedures requiring either high fluid flow rates or the introduction of relatively viscous fluids. The second, injectate lumen 40 is even more significant where fluid must be introduced or withdrawn at the same time the probe lumen is being used. The cross-section of the injectate lumen 40 is preferably crescent-shaped, with the cross-section of the lumen covering or extending around at least a quarter arc of the catheter body cross-section. The crescent shape allows for maximum fluid flow area within the catheter body 12 without interfering with the first lumen 36.

The third lumen 44 is preferably used for inflating and deflating the inflation balloon 14 to properly position the catheter, for example where the catheter is used as a thermodilution catheter. The fourth lumen 48 is preferably used for instrumentation, such as for passing thermistor wires or the like along the catheter to a point where a sensing device is located in the catheter.

The catheter body 12 of the present invention is preferably formed by any of several well known extrusion methods. The catheter body 12 may be fabricated from any of a variety of suitable materials, including, but not limited to, flexible polyvinyl chloride (PVC), polyurethane, nylon, or polypropylene. The catheter body 12 is also preferably coated with heparin.

In the preferred embodiment described herein, the catheter body 12 has an outer diameter of 0.101 inches centered on the central axis 50 of the catheter. The total cross-sectional area of the catheter body 12 is therefore approximately 0.008 square inches. The first lumen 36 preferably is circular with a diameter of 0.056 inches and includes within it the central axis 50. The cross-sectional area of the first lumen 36 is therefore approximately 0.0024 square inches, which equates to approximately thirty percent of the catheter body cross-sectional area. The cross-sectional area of the crescent-shaped second lumen 40 is approximately 0.0016 square inches, which is approximately twenty percent of the total cross-sectional area of the catheter body 12. The largest distance between oppositely arcing surfaces in the crescent shape is about 0.024 inches and the radius of curvature of the ends of the injectate lumen is about 0.010 inches. To optimize the available area that can be used for fluid flow, the injectate lumen in the preferred embodiment is symmetrically placed above the probe lumen and centered so that an imaginary vertical plane (vertical when viewing FIG. 2) through the central axis 50 and the central axis of the probe lumen bisects both the probe lumen and the injectate lumen. It should be understood, however, that where one or the other of the third or fourth lumens is omitted, the injectate lumen may be formed asymmetrically relative to a line through the central axis 50 and the central axis of the probe lumen. The third lumen 44 and the fourth lumen 48 are both preferably circular, and have a diameter of approximately 0.012 inches. Therefore, the cross-sectional areas of the third lumen 44 and the fourth lumen 48 are each approximately 0.0001 square inches, which equates to approximately one and one-half percent of the total cross-sectional area of the catheter body 12. The smallest dimension from any of the tureens radially to the outer edge of the catheter body is preferably 0.007 inches. The thickness of any wall between lumens is preferably at least 0.007 inches. The dimensions of the catheter body 12 and lumens given are preferred, but they are exemplary only of the preferred embodiment of the invention.

It should be understood that the cross-sectional configuration shown in FIG. 2 is preferred, and extends in the preferred embodiment substantially the entire length of the catheter. However, it should also be understood that the inflation lumen 44 terminates at the inflation balloon 14. It should also be understood that the injectate lumen may open at an injectate port 52 through the outer catheter wall at a suitable location near the distal end 22 along the length of the catheter body (FIG. 3). Where the catheter has an overall usable length of 110 centimeters, the injectate port 52 is typically located about 30 centimeters proximal of the distal end of the catheter, a standard distance for a thermodilution catheter. A thermistor 54 is exposed to the outside of the catheter approximately 4 centimeters proximal of the distal end.

Considering the distal-most portions of the catheter in more detail (FIGS. 4 and 5), fluid flow out the injectate port is created by placing an injectate lumen plug 56 in the injectate lumen 40. The plug 56 has a general transverse cross-section conforming to that of the injectate lumen and is sealed in place by a suitable biocompatible filler. The thermistor 54 is potted in an opening formed in the outer catheter surface. Preferably, the thermistor is potted in the injectate lumen since the injectate lumen downstream of the plug 56 is otherwise unused. Thermistor wires 58 from the fourth lumen 48 pass into the injectate lumen 40 through a cross-over 60 from the fourth lumen.

In order to reduce the volume of air in the unused and therefore vacant portion of the injectate lumen, namely the portion of the injectate lumen distal of the plug 56, a crescent shaped insert or rod 62 is inserted in the injectate lumen and fixed with a suitable adhesive 64 between the plug 56 and the cross-over 60. The rod is preferably formed from the same material as the catheter and preferably to provide the same flexibility as the catheter without the plug. A probe 66 is shown in FIGS. 4 and 5 and can be made from plastic, metal, plastic coated metal, composites or other suitable materials used in manufacturing probes, sensors or other instrumentation.

A hemostasis valve 67 is also shown in FIG. 3 through which the probe passes into the extension tube. An injection port may also be connected to the valve 67 through an appropriate stopcock, shown schematically at 67A, to which may be connected a conventional pressure sensor device, a fluid injection device, and the like.

The orientation of the lumens within the catheter body 12 accommodates the four lumens with the probe and injectate lumens having a relatively large cross-sectional area. As a result, the cross-sectional areas of the third and fourth lumens remain relatively small. In use, the probe and injectate lumens are filled with a liquid, with only the third and fourth lumens containing any appreciable air space. The relatively small quantity of air space in the third and fourth lumens minimizes undesirable attenuation of ultrasonic signals when an ultrasound probe is used within the probe lumen 36. Therefore, an ultrasound probe used in the probe lumen of the preferred embodiment produces a more accurate result.

The design of the catheter body 12 also provides the advantage of structural integrity. The configuration of the lumens and the thickness of the lumen walls contributes to the structural integrity and strength of the catheter body, thereby minimizing the possibility that the catheter may be constricted or crushed during use.

More specifically, in the preferred embodiment of the invention, a substantial portion of each of the lumen walls preferably has a thickness greater than the shortest distance between the first wall of the probe lumen and the outer edge of the catheter body 12. Therefore, any possibility that the catheter body 12 may be pressed or any lumens may be constricted when the catheter is passed through a seal on an outer transport catheter is minimized.

In a further preferred embodiment of the invention, a transport catheter includes the probe and injectate lumens 36 and 40, respectively but omits the inflation balloon and the inflation lumen. Omitting the inflation lumen allows the injectate lumen to be made larger if necessary by increasing the arcuate length or arcuate extent of the injectate lumen, thereby increasing its cross-sectional area and its flow characteristics. The catheter of this alternative preferred configuration has a number of applications, similar to those of the embodiment of FIG. 1, including sensing, fluid injection and sampling and the like. The probe lumen is still preferably circular in cross-section and occupies a substantial portion of the catheter cross-section. The injectate lumen is also preferably crescent shaped and occupies as much of the remaining cross-sectional area of the catheter as necessary to achieve high fluid flow in the lumen or to allow efficient introduction of more viscous fluids.

An alternative embodiment of a catheter 68 (FIG. 6) includes a first lumen exit port 70 proximal of the distal end of the catheter approximately 30 centimeters, in the embodiment where the catheter length is 110 centimeters. A round lumen plug 74 is sealed in the circular first lumen 76 to direct fluid from the first lumen externally of the catheter. The port 70 allows infusion of a fluid through the first lumen into the body cavity at a relatively high flow rate. The cross-sectional area of the port 70 is preferably the same as that of the first lumen. The cross-sectional configuration of the catheter is preferably the same as that shown in FIG. 2 to allow the relatively high fluid flow rates in the first lumen and in the injectate lumen, while also having a relatively small inflation lumen 78 and a relatively small fourth lumen. The injectate lumen 80 preferably has the same cross-sectional configuration as the preferred cross-sectional configuration of the injectate lumen 40 described above with respect to FIG. 2. A portion of the bottom surface 80 of the injectate lumen is shown as though the segmented sectional view of FIG. 6 were taken off center. In a preferred form of the catheter, thermistor wires from the fourth lumen cross over through the wall between the first and fourth lumens. The wires extend into the first lumen near the distal end of the catheter to a thermistor that is exposed to the outside of the catheter through the external wall of the first lumen.

Having thus described exemplary embodiments of the present invention, it should be noted by those skilled in the art that the within disclosures are exemplary only and that various other alternatives, adaptations and modifications may be made within the scope of the invention. Thus by way of example, but not of limitation, the relative orientation and dimensions of the lumens within the catheter body may be altered. Accordingly, it is to be understood that the present invention is not limited to the precise construction as shown in the drawings and described hereinabove.

We claim:

1. A catheter for accepting probes and for introducing fluid through the catheter and into a body cavity, the catheter comprising:
    a catheter body circular in transverse cross-section and defining a central axis and having a continuous outer edge surface with a corresponding maximum outer dimension and having a proximal end and a distal end and a distal inflation balloon,
    said catheter body having walls defining, in transverse cross-section, lumens including a first wall defining a first lumen having a first cross-sectional dimension approximately half the maximum outer dimension of the catheter body wherein a substantial portion of the first wall has a thickness greater than shortest distance between the first wall and the outer edge of the catheter body and wherein the first lumen encloses the central axis, and a second wall defining a second, curved lumen wherein the second lumen occupies at least a quarter of an arc around the catheter body, and a third wall defining a third, inflation lumen for inflating and deflating the inflation balloon.

2. The catheter of claim 1 further comprising a fourth wall defining a fourth lumen for accepting a portion of a sensing instrument for the catheter.

3. The catheter of claim 2 wherein the area of the fourth lumen is approximately 0.0001 square inches.

4. The catheter of claim 1 wherein the catheter has an outer wall surface portion with an outer curvature and the first lumen has a circular transverse cross-sectional configuration and the curved lumen has an outer wall surface adjacent the catheter outer wall surface portion and having a curvature approximating the curvature of the catheter outer wall surface portion.

5. The catheter of claim 1 wherein the first lumen and the curved lumen are positioned with respect to each other so as to be each bisected by a plane extending longitudinally of the catheter.

6. The catheter of claim 1 wherein a substantial portion of the first wall and the second wall has a thickness greater than the shortest distance between the first wall and the outer edge of the catheter body.

7. The catheter of claim 1 wherein the maximum outer dimension is approximately 0.101 inches.

8. The catheter of claim 1 wherein the cross-sectional area of the first lumen is approximately 0.002 square inches.

9. The catheter of claim 1 wherein the cross-sectional area of the second lumen is approximately 0.0016 square inches.

10. The catheter of claim 1 wherein the area of the third lumen is approximately 0.0001 square inches.

11. An elongated flexible transport catheter having a round catheter body, and further having at least two independent lumens extending longitudinally from a catheter proximal end to a catheter distal end, wherein the lumens include:
    a first lumen defined by a first wall, wherein a substantial portion of the first wall has a thickness greater than shortest distance between the first wall and the outer edge of the catheter body and wherein the first lumen has a circular cross-sectional area of approximately thirty percent of the total cross-sectional area of the catheter body;
    a second lumen having a curved cross-sectional area of approximately twenty percent of the total cross-sectional area of the catheter body;

a third lumen having a cross-sectional area of approximately one and one-half percent of the total cross-sectional area of the catheter body; and a fourth lumen having a cross-sectional area of approximately one and one-half percent of the total cross-sectional area of the catheter body.

12. The catheter of claim 11 further including a distal inflation balloon and wherein the third lumen is used for inflating and deflating the inflation balloon.

13. The catheter of claim 11 wherein the fourth lumen is dimensioned to receive part of a sensing instrument for the catheter.

14. A catheter for accepting probes and for introducing fluid through the catheter and into a body cavity, the catheter comprising:

a round catheter body having an outer edge with a maximum outer diameter and a radius and having a proximal end and a distal end and further having walls defining, in transverse cross-section, a plurality of lumens extending longitudinally through the catheter body including a first wall defining a first circular lumen having a first diameter approximating the radius of the catheter body, wherein a substantial portion of the first wall has a thickness greater than the shortest distance between the first wall and the outer edge of the catheter body, a second wall defining a curved lumen wherein the lumen occupies at least a quarter of an arc around the catheter body, a third wall defining an inflation lumen, and a fourth wall defining an instrument lumen for passing a portion of an instrument along the lumen;

a plurality of extension tubes, each having a first end and a second end, each of the second ends being coupled to a respective lumen wall for permitting access to the respective lumen; and an inflation balloon coupled to the distal end of the catheter body, wherein the inflation lumen is used for inflating and deflating the balloon in order to properly positioning the catheter.

15. The catheter of claim 14 wherein the first end of each of the extension tubes is coupled to a respective one of a plurality of threaded hubs.

16. A catheter for accepting probes and for introducing fluid through the catheter and into a body cavity, the catheter comprising:

a round catheter body having a central axis and a proximal end and a distal end and further having internal walls defining, in transverse cross-section, a plurality of lumens extending longitudinally a substantial distance through the catheter body including a first wall defining a first, circular lumen encircling the central axis, wherein a substantial portion of the first wall has a thickness greater than shortest distance between the first wall and the outer edge of the catheter body, a second wall defining a second, curved lumen, and a third wall defining an inflation lumen;

a plurality of extension tubes, each having a first end and a second end, each of the second ends being coupled to a respective lumen wall for permitting access to the respective lumen; and an inflation balloon coupled to the distal end of the catheter body, wherein the inflation lumen is used for inflating and deflating the balloon.

17. The catheter of claim 16 wherein the second lumen comprises an injectate lumen and wherein the catheter further comprises an injectate port opening the injectate lumen to the outside of the catheter and an injectate plug in the injectate lumen distal of the injectate port.

18. The catheter of claim 17 further comprising an insert in the injectate lumen extending distally of the injectate plug to displace air from the injectate lumen.

19. The catheter of claim 18 further comprising a filler between the insert and the wall of the injectate lumen.

20. The catheter of claim 16 further comprising fourth wall defining a fourth lumen for passing instrumentation along the lumen.

21. The catheter of claim 20 further comprising a thermistor exposed to the outside of the catheter and positioned proximal of the inflation balloon.

22. The catheter of claim 16 wherein the catheter is round and has an outer diameter and the first circular lumen has a diameter approximately half the outer diameter of the catheter.

23. The catheter of claim 22 wherein the curved lumen curves through an arc of more than a quarter of a full circle passing through the curved lumen.

* * * * *